United States Patent [19]
Nakamura et al.

[11] Patent Number: 5,750,516
[45] Date of Patent: May 12, 1998

[54] PHOSPHORIC DIESTER

[75] Inventors: Masayuki Nakamura, Himeji; Kazumi Ogata, Toyonaka; Takahiro Sakaue, Itami; Noriko Saito, Minoo; Masahito Iemura, Kyoto, all of Japan

[73] Assignee: Senju Pharmaceutical Co., Ltd., Osaka, Japan

[21] Appl. No.: 724,509

[22] Filed: Sep. 30, 1996

[30] Foreign Application Priority Data

Oct. 13, 1995 [JP] Japan .................. 7-265615

[51] Int. Cl.$^6$ .............. A61K 31/665; A61K 31/355; C07F 9/06; C07F 9/28
[52] U.S. Cl. .............. 514/100; 514/458; 549/220; 549/222; 549/408; 549/477
[58] Field of Search .............. 549/220, 222, 549/408, 477; 514/100, 458

[56] References Cited

U.S. PATENT DOCUMENTS

| | | | |
|---|---|---|---|
| 4,564,686 | 1/1986 | Ogata | 549/220 |
| 4,948,786 | 8/1990 | Shimamoto et al. | 514/100 |
| 5,306,713 | 4/1994 | Suetsugu et al. | 514/100 |

FOREIGN PATENT DOCUMENTS 0 324 387  7/1989  European Pat. Off.
0 430 045  6/1991  European Pat. Off.

*Primary Examiner*—C. Warren Ivy
*Assistant Examiner*—Evelyn Huang
*Attorney, Agent, or Firm*—Wenderoth, Lind & Ponack

[57] ABSTRACT

This invention provides a phosphoric diester of formula (I) which is available on di-esterification of phosphoric acid with L-ascorbic acid involving its 5-hydroxyl group and tocopherol involving its hydroxyl group or a pharmacologically acceptable salt thereof.

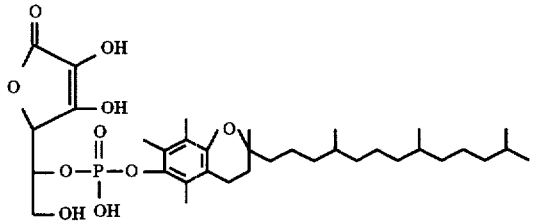

(I)

The compound of the invention can be used with advantage as an antioxidant (radical-scavenging) agent and a prophylactic and therapeutic agent for ischemic organ disorders (e.g. myocardial infarction, heart failure, arrhythmia, cerebral infarction, stroke (cerebral apoplexy), renal failure, etc.).

6 Claims, No Drawings

5,750,516

PHOSPHORIC DIESTER

BACKGROUND OF THE INVENTION

1. Field of the Invention

The present invention relates to a novel and useful phosphoric diester compound, a process for producing the diester compound, and an antioxidant composition and a prophylactic and therapeutic composition for ischemic organ disorders each comprising said diester compound.

2. Description of the Prior Art

Oxygen is not only an indispensable substance for living matter but also a toxic substance causing oxidation disorders. In living things, most of available oxygen functions as an electron acceptor in the energy metabolic pathways for the maintenance of life. However, oxygen can be an etiologic factor in a variety of functional disorders of tissues such as impairment of biological membranes due to production of lipid peroxides, disturbance of the redox system and injury of normal tissues associated with the overdefending activity of neutrophils [Hiroyuki Shimazaki: The Lipid, 3(3), 222–228 (1992-4)].

As drugs capable of suppressing such reactions due to activated oxygen (active oxygen), especially those drugs which inhibit oxidation of membrane lipids to stabilize the membranes, L-ascorbic acid and dl-α-tocopherol are known. However, these compounds have been found to be inadequate for implementation as pharmaceutical products in terms of potency, water solubility, and stability.

Moreover, the phosphoric diester available on di-esterification of phosphoric acid with L-ascorbic acid involving its 2-hydroxyl group and tocopherol involving its hydroxyl group has been reported to have prophylactic and therapeutic efficacy against ischemic organ impairments because of its antioxidant properties (U.S. Pat. No. 4,948,786).

Under the circumstances the inventors of the present invention did much research to find a compound structurally analogous with said diester but having still more potent antioxidant activity and higher water solubility. As a result, they succeeded in synthesizing a phosphoric diester of the following general formula (I) and its pharmacologically acceptable salt and found that these compounds have very potent antioxidant activity and prophylactic and therapeutic efficacy against ischemic organ disorders as well as improved water solubility. The present invention has been developed on the basis of the above finding.

SUMMARY OF THE INVENTION

The present invention relates to (1) a phosphoric diester of formula (I) which is available on di-esterification of phosphoric acid with L-ascorbic acid involving its 5-hydroxyl group and tocopherol involving its hydroxyl group or a pharmacologically acceptable salt thereof [hereinafter referred to as compound (I)];

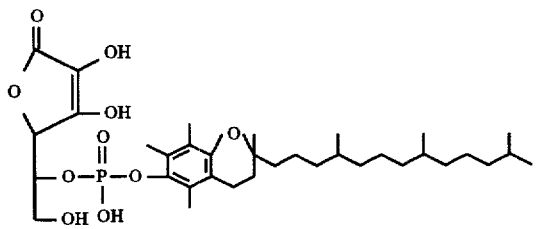

(2) compound (I) wherein said tocopherol is α-tocopherol;

(3) a process for producing compound (I);

(4) an antioxidant composition comprising compound (I); and (5) a prophylactic and therapeutic composition for ischemic organ disorders which comprises compound (I).

DETAILED DESCRIPTION OF THE INVENTION

The salt of compound (I) includes any and all pharmacologically acceptable salts, thus including alkali metal salts such as sodium salt, potassium salt, etc. and alkaline earth metal salts such as calcium salt and magnesium salt.

Compound (I) can be synthesized in accordance with the following reaction schema or any version thereof. Thus, compound (I) can be synthesized by reacting compound (II) with compound (III) to give compound (IV) and deprotecting compound (IV).

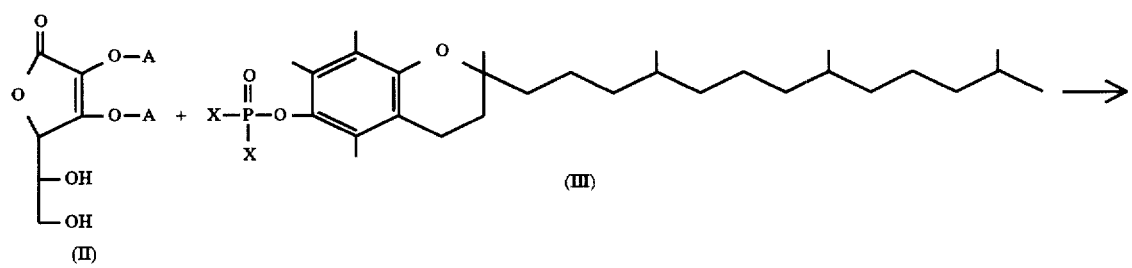

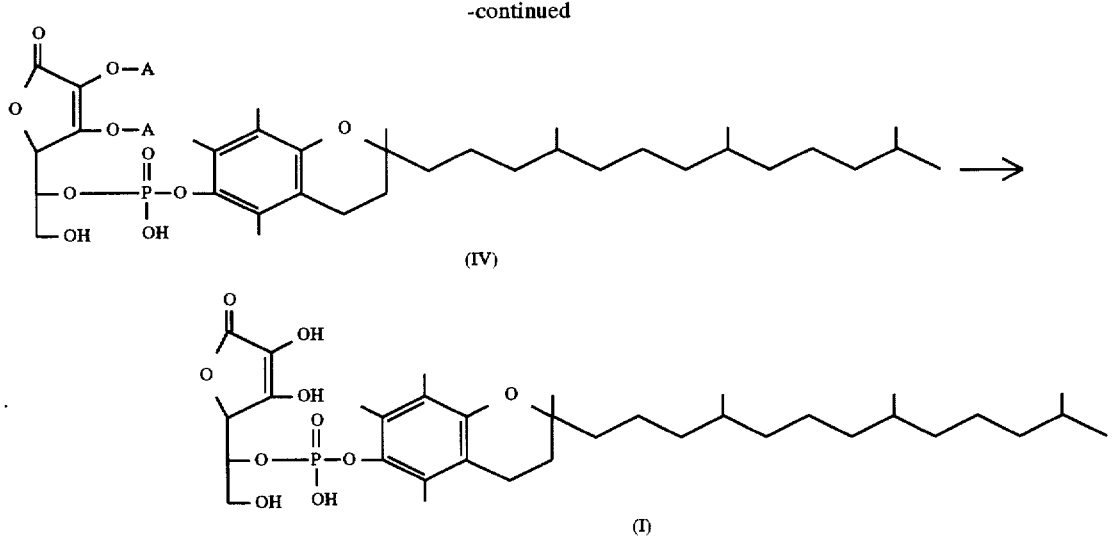

In the above reaction schema, the compound of general formula (II) is ascorbic acid whose hydroxyl groups in 2- and 3-positions have been protected and each A represents a hydroxy-protecting group, which may for example be benzyl or methoxymethyl.

Referring, further, to the above reaction schema, compound (III) is a tocopheryl dihalogen phosphate and each X represents halogen such as chlorine, bromine or iodine. Tocopherol may for example be α-tocopherol, β-tocopherol, γ-tocopherol, or δ-tocopherol and any of them can be used with advantage for the purposes of the present invention. The preferred halophosphorylating agent includes phosphorus oxytrichloride and phosphorus oxytribromide, among others.

The reaction of compound (II) with compound (III) to give compound (IV) [wherein A is as defined above] is conducted in the common solvent such as tetrahydrofuran, dioxane, dichloromethane, acetone or the like. However, any other organic solvent that does not interfere with the reaction can likewise be employed. In this reaction, an organic base is used as the dehalogenating agent. The base that can be used includes but is not limited to pyridine, diethylamine, trimethylamine, and triethylamine. The reaction temperature is not so critical but the reaction is generally conducted under cooling, at ambient temperature, or under mild heating. This reaction goes to completion in about 4 hours at 50° C.

The reaction for conversion of compound (IV) to compound (I) can be carried out by a suitable method as selected from among known methods according to the kind of protective groups used for protecting the hydroxyl groups of ascorbic acid. Taking the case in which the protective group is benzyl, for instance, hydrogen gas is bubbled through the reaction mixture including palladium (5%)-on-carbon (catalytic reduction) or in the case where the protective group is methoxymethyl, a hydrolysis reaction is carried out using an ordinary acid such as hydrochloric acid, sulfuric acid or phosphoric acid to give compound (I). As the reaction solvent, any of the common solvents such as ethyl acetate, methanol, ethanol, water, tetrahydrofuran, dioxane, dichloromethane, acetone, etc. can be employed. Any other organic solvent that does not interfere with the reaction can also be employed. The reaction temperature is not so critical but the reaction is generally carried out under cooling, at ambient temperature, or under mild heating. The reaction goes to completion in about 16 hours at ambient temperature.

Compound (I), thus obtained, is a novel compound never heretofore documented and has potent antioxidant (radical scavenging) activity and high water solubility. As such, compound (I) does effectively inhibit production of peroxylipids and in vivo oxidation reactions inducing the crosslinking of protein so that it can be used with advantage as a prophylactic and therapeutic drug for ischemic organ diseases (such as myocardial infarction, heart failure, arrhythmia, cerebral infarction, stroke (cerebral apoplexy), renal failure, etc.), cataract, and other diseases or as an antiaging drug. Furthermore, compound (I) is expected to find application as a prophylactic and therapeutic drug for climacteric disturbance or an antiinflammatory drug. In addition, compound (I) can be formulated into cosmetic and food products.

When compound (I) is put to use as a pharmaceutical preparation for the above-mentioned diseases, it can be administered orally or parenterally, either topically or systemically, in any of the usual dosage forms including tablets, powders, granules, capsules, syrups, injections, eyedrops, etc. These dosage forms may contain the known pharmacologically acceptable additives which are generally used in the pharmaceutical industry, such as the carrier, excipient, diluent, buffer, isotonizing agent, preservative, stabilizer, emulsifier, thickener, chelating agent, pH control agent, solubilizer, and surfactant in suitable proportions.

When compound (I) is used as a cosmetic material, it can be formulated into creams, lotions and toilet water for the purpose of absorbing ultraviolet light, for skin care, or stabilizing other cosmetic ingredients. When this compound is incorporated in cosmetic products, the ingredients which are generally used in such products can be added in suitable proportions.

For application of compound (I) as a drug, the dosage depends on the particular species of compound, the type of disease to be treated, the route of administration, the symptoms to be controlled, the patient's clinical status, age and other factors. Taking an injection as an example, about 0.1 mg to about 30 mg per dose can be administered once a day to the average adult. In the case of an oral preparation, about 1 mg to about 100 mg can be administered a few times a day to the average adult. For the treatment of cataract in an adult patient, a few drops of an ophthalmic preparation of about 0.01–5 (w/v) %, preferably about 0.05–2 (w/v) %, concentration can be instilled several times daily.

For use of compound (I) as a cosmetic ingredient, its concentration should be dependent on the species of compound, the type of cosmetic product, and the objective of formulation but the recommended level of addition is generally about 0.001–5 (w/w) % and preferably about 0.005–0.2 (w/w) %.

For addition of compound (I) as an antioxidant to food, the proper level of addition is generally about 0.001–5 (w/w) % and preferably about 0.005–0.2 (w/w) %, although the specific level should vary with different species of the compound and kinds of substrate foods.

Depending on the objective and needs, two or more species of the compound of the invention can be used in one and the same unit dosage.

EXAMPLES

The following examples and formulation examples are intended to describe the present invention in further detail.

Example 1

Synthesis of L-Ascorbic Acid 5-[3,4-Dihydro-2,5,7,
8-tetramethyl-2-(4,8,12-trimethyltridecyl)-2H-1-
benzopyran-6-yl Hydrogen Phosphate]

(1) Synthesis of 2,3-O-dibenzyl-5,6-O-isopropylidene-L-ascorbic acid (known compound)

In a mixture of N,N-dimethylformamide (300 ml) and tetrahydrofuran (250 ml) was dissolved 100 g of 5,6-O-isopropylidene-L-ascorbic acid followed by addition of 128 g of potassium carbonate. While this mixture was held at a temperature not over 30° C. with stirring, 206 g of benzyl bromide was added dropwise. This reaction mixture was neutralized by adding 60 ml of acetic acid and 800 ml of purified water and extracted with 800 ml of dichloromethane. The extract was washed with 400 ml of saturated aqueous sodium hydrogen carbonate solution, dehydrated over anhydrous magnesium sulfate, and concentrated under reduced pressure. The residue was recrystallized from 500 ml of ethyl acetate and 50 ml of isopropyl ether and the crystal crop was dried in vacuo to provide 80 g of 2,3-O-dibenzyl-5,6-O-isopropylidene-L-ascorbic acid.

(2) Synthesis of 2,3-O-dibenzyl-L-ascorbic acid (known compound)

In a mixture of tetrahydrofuran (250 ml) and diluted hydrochloric acid (200 ml) was dissolved 80 g of the above 2,3-O-dibenzyl-5,6-O-isopropylidene-L-ascorbic acid and the solution was stirred at 40°–45° C. for 2 hours. After completion of the reaction, the reaction mixture was diluted with 300 ml of purified water and extracted with 600 ml of ethyl acetate. The extract was washed with saturated saline solution and the ethyl acetate layer was dehydrated over anhydrous magnesium sulfate and concentrated under reduced pressure. The residue was recrystallized from 80 ml of ethyl acetate and 600 ml of hexane and the crystal crop was dried in vacuo to provide 70 g of 2,3-O-dibenzyl-L-ascorbic acid.

(3) Synthesis of L-ascorbic acid 5-[3,4-dihydro-2,5,7,8-tetramethyl-2-(4,8,12-trimethyltridecyl)-2H-1-benzopyran-6-yl hydrogen phosphate] potassium In 200 ml of tetrahydrofuran was dissolved 20 g of the above 2,3-O-dibenzyl-L-ascorbic acid followed by addition of 10 g of pyridine. To the above solution of 2,3-O-dibenzyl-L-ascorbic acid, a solution of 28 g of tocopheryl phosphorodichloridate in 50 ml of tetrahydrofuran was added dropwise and the reaction was conducted at 50° C. for 4 hours. After completion of the reaction, the reaction mixture was filtered and the filtrate was diluted with 200 ml of diluted hydrochloric acid under ice-cooling. After stirring, the mixture was extracted with 300 ml of ethyl acetate and the extract was washed with 300 ml of saturated aqueous sodium hydrogen carbonate solution and dehydrated over anhydrous magnesium sulfate. The ethyl acetate was then distilled off under reduced pressure. The residue was dissolved in 300 ml of ethyl acetate and, after addition of 4.0 g of palladium (5%)-on-carbon, hydrogen gas was bubbled through the solution at atmospheric pressure for about 16 hours. After completion of the catalytic reduction reaction, the palladium-on-carbon was filtered off and the filtrate was washed with 3.5% hydrochloric acid and further with saturated aqueous sodium hydrogen carbonate solution. The ethyl acetate layer was dehydrated over anhydrous magnesium sulfate and the ethyl acetate was distilled off under reduced pressure to give 26 g of oil. This oil, 200 mg, was fractionated by HPLC under the conditions indicated below for a total of 6 times. The principal fractions were pooled and concentrated to ⅓ volume and extracted using the same volume of ethyl acetate and purified water. The ethyl acetate layer was dehydrated over anhydrous magnesium sulfate and the ethyl acetate was distilled off under reduced pressure to give a colorless oil. This oil was dissolved in 40 ml of isopropyl alcohol and adjusted to pH 6 with 1N-potassium hydroxide/isopropyl alcohol for crystallization. The crystals were centrifugally collected and dried in vacuo to provide 90 mg of the objective L-ascorbic acid 5-[3,4-dihydro-2,5,7,8-tetramethyl-2-(4,8,12-trimethyltridecyl)-2H-1-benzopyran-6-yl hydrogen phosphate] potassium.

(HPLC conditions for fractionation)

Column: YMC-Pack ODS S-5 20×250 mm

Mobile phase: Dissolve 0.4 g of crystalline sodium dihydrogen phosphate, 0.3 g of sodium chloride, and 11.2 g of sodium perchlorate in 200 ml of water, add 500 ml of methanol and 450 ml of acetonitrile to the solution, and adjust the mixture to pH 4 with phosphoric acid.

Flow rate: 20 ml/min.

Wavelength: 225 nm IR ($cm^{-1}$, KBr) 3405 (O—H), 2927 (chain, C—H), 1764 (C=O), 1681 (C=C), 1461 (C—H), 1087 (P—O—C).

$^1$H-NMR ($CD_3OD$ 270 MHz) δ: 0.84–0.89 (m, 12H), 1.11–1.58 (m, 21H), 1.20 (s, 3H), 1.74–1.80 (m, 2H), 2.03 (s, 3H), 2.15 (s, 3H), 2.19 (s, 3H), 2.58 (t, 2H), 3.67 (dd, 1H), 3.85 (dd, 1H), 4.56–4.65 (m, 1H), 4.96 (dd, 1H).

$^{13}$C-NMR ($CD_3OD$ 67.5 MHz) δ: 12.1, 13.5, 14.4, 20.1, 20.2, 21, 8, 22.1, 23.1, 24.2, 25.4, 25.9, 29.2, 32.8, 33.9, 38.3, 38.8, 40.6, 40.8, 62.4, 64.7, 75.9, 76.3, 118.4, 120.3, 123.2, 127.0, 128.8, 144.2, 144.3, 148.9, 154.7, 173.5. SIMS-MS m/s 707 $(M+H)^+$

Example 2

Effect of 5-Ascorbic Acid 5-[3,4-Dihydro-2,5,7,8-
tetramethyl-2-(4,8,12-trimethyltridecyl)-2H-1-
benzopyran-6-yl Hydrogen Phosphate] Potassium
on Autooxidation of the Rat Brain Homogenate Rats of Wistar strain (male, 11 weeks old) were used. The animal was decapitated and the brain was enucleated and homogenized in 4 ml/gram of 50 mM phosphate-buffered saline (pH 7.4). The homogenate was centrifuged (1000 g, 10 min.) and the supernatant was harvested. The test solution was set to $10^{-7}$–$10^{-4}$M (dissolved at a final ethanol concentration of 1%). To 100 μl of the test solution was added 200

μl of the brain homogenate as well as 700 μl of phosphate-buffered saline and the mixture was incubated at 37° C. for 30 minutes for lipid peroxidation. The reaction was stopped with 200 μl of 35% perchloric acid and centrifuged (1300 g, 10 min.) and the MDA (malondialdehyde) value of the supernatant was determined by the TBA (thiobarbituric acid) method.

The results are shown in Table 1.

TABLE 1

Effect of the present compound on lipid peroxidation in rat brain homogenate

| Concentration (M) | Inhibition (%) |
|---|---|
| $10^{-4}$ | 98.5 |
| $10^{-5}$ | 98.7 |
| $10^{-6}$ | 93.3 |
| $10^{-7}$ | 24.7 |

It is apparent from Table 1 that L-ascorbic acid 5-[3,4-dihydro-2,5,7,8-tetramethyl-2-(4,8,12-trimethyltridecyl)-2H-1-benzopyran-6-yl hydrogen phosphate] potassium inhibits autooxidation of the rat brain homogenate to a remarkable extent.

Example 3

The DPPH (1,1-Diphenyl-2-picrylhydrazyl) Radical Scavenging Action of L-ascorbic Acid 5-[3,4-Dihydro-2,5,7,8-tetramethyl-2-(4,8,12-trimethyltridecyl)-2H-1-benzopyran-6 -yl Hydrogen Phosphate] Potassium To 2.7 ml of 0.11 mM-DPPH/ethanol was added 300 μl of the test solution and the mixture was stirred and allowed to stand for 20 minutes. Then, the absorbance was measured at 517 nm. The radical scavenging effect (%) of each test solution was calculated by means of the following equation.

$$\text{Radical scavaging effect (\%)} = \frac{\text{(absorbance of control} - \text{absorbance of test solution)}}{\text{absorbance of control}} \times 100$$

The results are shown in Table 2.

TABLE 2

Scavenging Effect of the present compound on DPPH radical

| Concentration (M) | Inhibition (%) |
|---|---|
| $10^{-3}$ | 96.7 |
| $10^{-4}$ | 97.3 |
| $5 \times 10^{-5}$ | 71.7 |
| $10^{-5}$ | 13.1 |

It is apparent from Table 2 that L-ascorbic acid 5-[3,4-dihydro-2,5,7,8-tetramethyl-2-(4,8,12-trimethyltridecyl)-2H-1-benzopyran-6-yl hydrogen phosphate] potassium scavenges DPPH radicals to a remarkable extent.

Formulation Example 1 Injection

| | |
|---|---|
| L-Ascorbic acid 5-[3,4-dihydro-2,5,7,8-tetramethyl-2-(4,8,12-trimethyltridecyl)-2H-1-benzopyran-6-yl hydrogen phosphate] potassium | 20 g |

-continued

| | |
|---|---|
| Glucose | 5 g |
| Distilled water for injection | to make 100 ml |

Using the above components, an injection is prepared by the routine procedure.

Formulation Example 2 Ophthalmic solution

| | |
|---|---|
| L-Ascorbic acid 5-[3,4-dihydro-2,5,7,8-tetramethyl-2-(4,8,12-trimethyltridecyl)-2H-1-benzopyran-6-yl hydrogen phosphate] potassium | 0.5 g |
| Boric acid | 1.8 g |
| Benzalkonium chloride | 0.005 g |
| Sodium hydroxide | q.s. pH 7.3 |

The above components are mixed in the routine manner to provide an ophthalmic solution.

Formulation Example 3 Oral tablets

| | |
|---|---|
| L-Ascorbic acid 5-[3,4-dihydro-2,5,7,8-tetramethyl-2-(4,8,12-trimethyltridecyl)-2H-1-benzopyran-6-yl hydrogen phosphate] potassium | 100 mg |
| Lactose | 80 mg |
| Starch | 17 mg |
| Magnesium stearate | 3 mg |

The above components per tablet are compressed in the routine manner to provide tablets.

Formulation Example 4 Toilet water

| | |
|---|---|
| L-Ascorbic acid 5-[3,4-dihydro-2,5,7,8-tetramethyl-2-(4,8,12-trimethyltridecyl)-2H-1-benzopyran-6-yl hydrogen phosphate] potassium | 1.0 g |
| Citric acid | 0.1 g |
| Glycerin | 5.0 g |
| Ethanol | 8.0 ml |
| Methyl p-hydroxybenzoate | 0.1 g |
| Sterilized pure water | to make 100 ml |

Using the above components, a toilet water is prepared in the routine manner.

Formulation Example 5 Cosmetic cream

| | |
|---|---|
| L-Ascorbic acid 5-[3,4-dihydro-2,5,7,8-tetramethyl-2-(4,8,12-trimethyltridecyl)-2H-1-benzopyran-6-yl hydrogen phosphate] potassium | 1.0 g |
| Stearic acid | 2.0 g |
| Stearyl alcohol | 7.0 g |
| Squalane | 5.0 g |
| Octyldodecanol | 6.0 g |
| Polyoxyethylene(15) cetyl ether | 3.0 g |
| Glycerin monostearate | 2.0 g |
| Propylene glycol | 5.0 g |
| Methyl p-hydroxybenzoate | 0.2 g |
| Propyl p-hydroxybenzoate | 0.1 g |
| Sterilized pure water | 68.7 g |

The above components are mixed to provide a cosmetic cream.

Compound (I) according to the present invention has potent antioxidant (radical-scavenging) activity and high water-solubility and can, therefore, be used with advantage as a prophylactic and therapeutic agent for ischemic organ diseases (e.g. myocardial infarction, heart failure, arrhythmia, cerebral infarction, stroke (cerebral apoplexy), renal failure, etc.), cataract, and other diseases or as an antiaging drug. Moreover, compound (I) is expected to find application as a prophylactic and therapeutic agent for climacteric disturbance or as an antiinflammatory drug. Compound (I) is further of value as a UV-absorbing, skin conditioning ingredient in cosmetic products, as a stabilizer for other cosmetic materials, or even as a food additive.

What is claimed is:

1. A phosphoric diester of formula (I) which is available on di-esterification of phosphoric acid with L-ascorbic acid involving its 5-hydroxyl group and tocopherol involving its hydroxyl group or a pharmacologically acceptable salt thereof.

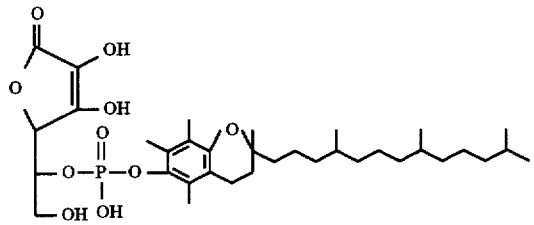
(I)

2. The phosphoric diester or pharmacologically acceptable salt according to claim 1 wherein said tocopherol is α-tocopherol.

3. An antioxidant composition comprising the phosphoric diester or pharmacologically acceptable salt of claim 1.

4. A prophylactic and therapeutic composition for ischemic organ disorders which comprises the phosphoric diester or pharmacologically acceptable salt of claim 1.

5. A method of inhibiting the oxidation of an oxidation-susceptible compound which comprises contacting the compound with an effective amount of the phosphoric diester or pharmacologically acceptable salt as defined in claim 1.

6. A method for the prophylaxis and treatment of ischemic organ disorder which comprises administering to a patient in need thereof an effective amount of the phosphoric diester or pharmacologically acceptable salt as defined in claim 1.

* * * * *